United States Patent
Wu (10) Patent No.: US 7,823,263 B2
(45) Date of Patent: Nov. 2, 2010

(54) METHOD OF REMOVING STENT ISLANDS FROM A STENT

(75) Inventor: Patrick P. Wu, Mountain View, CA (US)

(73) Assignee: Abbott Cardiovascular Systems Inc., Santa Clara ( * ) Notice: Subject to any disclaimer, the term of this patent is extended or adjusted under 35 U.S.C. 154(b) by 784 days.

(21) Appl. No.: 11/825,985

(22) Filed: Jul. 9, 2007

(65) Prior Publication Data
US 2008/0033529 A1  Feb. 7, 2008

Related U.S. Application Data

(60) Provisional application No. 60/830,208, filed on Jul. 11, 2006.

(51) Int. Cl.
*B23P 17/02* (2006.01)

(52) U.S. Cl. .................... 29/426.4; 29/557; 264/345

(58) Field of Classification Search ............... 29/421.1, 29/426.4, 426.5, 557, 235, 282; 264/162, 264/345; 451/36, 37, 51, 61; 137/15.05
See application file for complete search history.

(56) References Cited

U.S. PATENT DOCUMENTS

| | | | |
|---|---|---|---|
| 3,476,463 A | 11/1969 | Kreuzer | |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |

(Continued)

FOREIGN PATENT DOCUMENTS

CN  1241442  1/2000

(Continued)

OTHER PUBLICATIONS

International Search Rep. for PCT/US2007/015777 filed Jul. 10, 2007, mailed Dec. 4, 2007, 6 pgs.

(Continued)

*Primary Examiner*—Jermie E Cozart
(74) *Attorney, Agent, or Firm*—Squire, Sanders & Dempsey LLP (57) ABSTRACT

A tool for removing islands from a stent is disclosed. The tool includes a tube with at least one exit hole in communication with the center of the tube, and the tube being connected to a pressurized fluid source. A stent island is located over the exit hole and is removed by the force of the exiting fluid from the exit hole.

16 Claims, 3 Drawing Sheets

U.S. PATENT DOCUMENTS

| | | |
|---|---|---|
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,886,870 A | 12/1989 | D'Amore et al. |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,061,281 A | 10/1991 | Mares et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,976 A | 1/1995 | Couch |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,486,546 A | 1/1996 | Mathiesen et al. |
| 5,500,013 A | 3/1996 | Buscemi et al. |
| 5,502,158 A | 3/1996 | Sinclair et al. |
| 5,507,799 A | 4/1996 | Sumiya |
| 5,514,379 A | 5/1996 | Weissleder et al. |
| 5,525,646 A | 6/1996 | Lundgren et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,565,215 A | 10/1996 | Gref et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,603,722 A | 2/1997 | Phan et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,656,186 A | 8/1997 | Mourou et al. |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,686,540 A | 11/1997 | Kakizawa |
| 5,693,085 A | 12/1997 | Buirge et al. |
| 5,700,286 A | 12/1997 | Tartaglia et al. |
| 5,700,901 A | 12/1997 | Hurst et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,770,609 A | 6/1998 | Grainger et al. |
| 5,780,807 A | 7/1998 | Saunders |
| 5,788,558 A * | 8/1998 | Klein .......................... 451/36 |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohtuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |

| Patent | Type | Date | Inventor |
|---|---|---|---|
| 5,874,101 | A | 2/1999 | Zhong et al. |
| 5,874,109 | A | 2/1999 | Ducheyne et al. |
| 5,874,165 | A | 2/1999 | Drumheller |
| 5,876,743 | A | 3/1999 | Ibsen et al. |
| 5,877,263 | A | 3/1999 | Patnaik et al. |
| 5,879,713 | A | 3/1999 | Roth et al. |
| 5,888,533 | A | 3/1999 | Dunn |
| 5,891,192 | A | 4/1999 | Murayama et al. |
| 5,897,955 | A | 4/1999 | Drumheller |
| 5,906,759 | A | 5/1999 | Richter |
| 5,914,182 | A | 6/1999 | Drumheller |
| 5,916,870 | A | 6/1999 | Lee et al. |
| 5,922,005 | A | 7/1999 | Richter et al. |
| 5,942,209 | A | 8/1999 | Leavitt et al. |
| 5,948,428 | A | 9/1999 | Lee et al. |
| 5,954,744 | A | 9/1999 | Phan et al. |
| 5,957,975 | A | 9/1999 | Lafont et al. |
| 5,965,720 | A | 10/1999 | Gryaznov et al. |
| 5,971,954 | A | 10/1999 | Conway et al. |
| 5,976,182 | A | 11/1999 | Cox |
| 5,980,564 | A | 11/1999 | Stinson |
| 5,980,928 | A | 11/1999 | Terry |
| 5,980,972 | A | 11/1999 | Ding |
| 5,981,568 | A | 11/1999 | Kunz et al. |
| 5,986,169 | A | 11/1999 | Gjunter |
| 5,997,468 | A | 12/1999 | Wolff et al. |
| 6,010,445 | A | 1/2000 | Armini et al. |
| 6,015,541 | A | 1/2000 | Greff et al. |
| 6,042,606 | A | 3/2000 | Frantzen |
| 6,042,875 | A | 3/2000 | Ding et al. |
| 6,048,964 | A | 4/2000 | Lee et al. |
| 6,051,648 | A | 4/2000 | Rhee et al. |
| 6,056,993 | A | 5/2000 | Leidner et al. |
| 6,060,451 | A | 5/2000 | DiMaio et al. |
| 6,066,156 | A | 5/2000 | Yan |
| 6,071,266 | A | 6/2000 | Kelley |
| 6,074,659 | A | 6/2000 | Kunz et al. |
| 6,080,177 | A | 6/2000 | Igaki et al. |
| 6,080,488 | A | 6/2000 | Hostettler et al. |
| 6,083,258 | A | 7/2000 | Yadav |
| 6,093,463 | A | 7/2000 | Thakrar |
| 6,096,070 | A | 8/2000 | Ragheb et al. |
| 6,096,525 | A | 8/2000 | Patnaik |
| 6,099,562 | A | 8/2000 | Ding et al. |
| 6,103,230 | A | 8/2000 | Billiar et al. |
| 6,107,416 | A | 8/2000 | Patnaik et al. |
| 6,110,188 | A | 8/2000 | Narciso, Jr. |
| 6,110,483 | A | 8/2000 | Whitbourne |
| 6,113,629 | A | 9/2000 | Ken |
| 6,117,979 | A | 9/2000 | Hendriks et al. |
| 6,120,536 | A | 9/2000 | Ding et al. |
| 6,120,904 | A | 9/2000 | Hostettler et al. |
| 6,121,027 | A | 9/2000 | Clapper et al. |
| 6,125,523 | A | 10/2000 | Brown et al. |
| 6,127,173 | A | 10/2000 | Eckstein et al. |
| 6,129,761 | A | 10/2000 | Hubbell |
| 6,129,928 | A | 10/2000 | Sarangapani et al. |
| 6,131,266 | A | 10/2000 | Saunders |
| 6,150,630 | A | 11/2000 | Perry et al. |
| 6,153,252 | A | 11/2000 | Hossainy et al. |
| 6,156,062 | A | 12/2000 | McGuinness |
| 6,159,951 | A | 12/2000 | Karpeisky et al. |
| 6,160,084 | A | 12/2000 | Langer et al. |
| 6,160,240 | A | 12/2000 | Momma et al. |
| 6,165,212 | A | 12/2000 | Dereume et al. |
| 6,166,130 | A | 12/2000 | Rhee et al. |
| 6,169,170 | B1 | 1/2001 | Gryaznov et al. |
| 6,171,609 | B1 | 1/2001 | Kunz |
| 6,174,330 | B1 | 1/2001 | Stinson |
| 6,177,523 | B1 | 1/2001 | Reich et al. |
| 6,183,505 | B1 | 2/2001 | Mohn, Jr. et al. |
| 6,187,045 | B1 | 2/2001 | Fehring et al. |
| 6,210,715 | B1 | 4/2001 | Starling et al. |
| 6,224,626 | B1 | 5/2001 | Steinke |
| 6,228,845 | B1 | 5/2001 | Donovan et al. |
| 6,240,616 | B1 | 6/2001 | Yan |
| 6,245,076 | B1 | 6/2001 | Yan |
| 6,245,103 | B1 | 6/2001 | Stinson |
| 6,248,344 | B1 | 6/2001 | Ylanen et al. |
| 6,251,135 | B1 | 6/2001 | Stinson et al. |
| 6,251,142 | B1 | 6/2001 | Bernacca et al. |
| 6,260,976 | B1 | 7/2001 | Endou et al. |
| 6,273,913 | B1 | 8/2001 | Wright et al. |
| 6,281,262 | B1 | 8/2001 | Shikinami |
| 6,284,333 | B1 | 9/2001 | Wang et al. |
| 6,287,332 | B1 | 9/2001 | Bolz et al. |
| 6,290,721 | B1 | 9/2001 | Heath |
| 6,293,966 | B1 | 9/2001 | Frantzen |
| 6,295,168 | B1 | 9/2001 | Hofnagle et al. |
| 6,303,901 | B1 | 10/2001 | Perry et al. |
| 6,312,459 | B1 | 11/2001 | Huang et al. |
| 6,327,772 | B1 | 12/2001 | Zadno-Azizi et al. |
| 4,733,665 | C2 | 1/2002 | Palmaz |
| 6,375,826 | B1 | 4/2002 | Wang et al. |
| 6,379,381 | B1 | 4/2002 | Hossainy et al. |
| 6,387,121 | B1 | 5/2002 | Alt |
| 6,388,043 | B1 | 5/2002 | Langer et al. |
| 6,395,326 | B1 | 5/2002 | Castro et al. |
| 6,409,761 | B1 | 6/2002 | Jang |
| 6,423,092 | B2 | 7/2002 | Datta et al. |
| 6,461,632 | B1 | 10/2002 | Gogolewski |
| 6,464,720 | B2 | 10/2002 | Boatman et al. |
| 6,475,779 | B2 | 11/2002 | Mathiowithz et al. |
| 6,479,565 | B1 | 11/2002 | Stanley |
| 6,485,512 | B1 | 11/2002 | Cheng |
| 6,492,615 | B1 | 12/2002 | Flanagan |
| 6,494,908 | B1 | 12/2002 | Huxel et al. |
| 6,495,156 | B2 | 12/2002 | Wenz et al. |
| 6,511,748 | B1 | 1/2003 | Barrows |
| 6,517,888 | B1 | 2/2003 | Weber |
| 6,521,865 | B1 | 2/2003 | Jones et al. |
| 6,527,801 | B1 | 3/2003 | Dutta |
| 6,537,589 | B1 | 3/2003 | Chae et al. |
| 6,539,607 | B1 | 4/2003 | Fehring et al. |
| 6,540,777 | B2 | 4/2003 | Stenzel |
| 6,554,854 | B1 | 4/2003 | Flanagan |
| 6,563,080 | B2 | 5/2003 | Shapovalov et al. |
| 6,563,998 | B1 | 5/2003 | Farah |
| 6,565,599 | B1 | 5/2003 | Hong et al. |
| 6,569,191 | B1 | 5/2003 | Hogan |
| 6,569,193 | B1 | 5/2003 | Cox et al. |
| 6,572,672 | B2 | 6/2003 | Yadav et al. |
| 6,574,851 | B1 | 6/2003 | Mirizzi |
| 6,582,472 | B2 | 6/2003 | Hart |
| 6,585,755 | B2 | 7/2003 | Jackson et al. |
| 6,592,614 | B2 | 7/2003 | Lenker et al. |
| 6,592,617 | B2 | 7/2003 | Thompson |
| 6,613,072 | B2 | 9/2003 | Lau et al. |
| 6,620,194 | B2 | 9/2003 | Ding et al. |
| 6,626,939 | B1 | 9/2003 | Burnside |
| 6,635,269 | B1 | 10/2003 | Jennissen |
| 6,645,243 | B2 | 11/2003 | Vallana et al. |
| 6,656,162 | B2 | 12/2003 | Santini, Jr. et al. |
| 6,664,335 | B2 | 12/2003 | Krishnan |
| 6,666,214 | B2 | 12/2003 | Canham |
| 6,667,049 | B2 | 12/2003 | Janas et al. |
| 6,669,723 | B2 | 12/2003 | Killion et al. |
| 6,676,697 | B1 | 1/2004 | Richter |
| 6,679,980 | B1 | 1/2004 | Andreacchi |
| 6,689,375 | B1 | 2/2004 | Wahlig et al. |
| 6,695,920 | B1 | 2/2004 | Pacetti et al. |
| 6,696,667 | B1 | 2/2004 | Flanagan |
| 6,706,273 | B1 | 3/2004 | Roessler |
| 6,709,379 | B1 | 3/2004 | Brandau et al. |
| 6,719,934 | B2 | 4/2004 | Stinson |
| 6,719,989 | B1 | 4/2004 | Matsushima et al. |

| | | |
|---|---|---|
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,780,261 B2 | 8/2004 | Trozera |
| 6,801,368 B2 | 10/2004 | Coufal et al. |
| 6,805,898 B1 | 10/2004 | Wu et al. |
| 6,818,063 B1 | 11/2004 | Kerrigan |
| 6,822,186 B2 | 11/2004 | Strassl et al. |
| 6,846,323 B2 | 1/2005 | Yip et al. |
| 6,852,946 B2 | 2/2005 | Groen et al. |
| 6,858,680 B2 | 2/2005 | Gunatillake et al. |
| 6,867,389 B2 | 3/2005 | Shapovalov et al. |
| 6,878,758 B2 | 4/2005 | Martin et al. |
| 6,891,126 B2 | 5/2005 | Matile |
| 6,899,729 B1 | 5/2005 | Cox et al. |
| 6,911,041 B1 | 6/2005 | Zscheeg |
| 6,913,762 B2 | 7/2005 | Caplice et al. |
| 6,926,733 B2 | 8/2005 | Stinson |
| 6,943,964 B1 | 9/2005 | Zhang et al. |
| 6,981,982 B2 | 1/2006 | Amstrong et al. |
| 6,981,987 B2 | 1/2006 | Huxel et al. |
| 7,022,132 B2 | 4/2006 | Kocur |
| 7,128,737 B1 | 10/2006 | Goder et al. |
| 7,163,555 B2 | 1/2007 | Dinh |
| 7,166,099 B2 | 1/2007 | Devens, Jr. |
| 7,226,475 B2 | 6/2007 | Lenz et al. |
| 2001/0044652 A1 | 11/2001 | Moore |
| 2002/0004060 A1 | 1/2002 | Heublein et al. |
| 2002/0065553 A1 | 5/2002 | Weber |
| 2002/0111590 A1 | 8/2002 | Davila et al. |
| 2002/0190038 A1 | 12/2002 | Lawson |
| 2003/0033001 A1 | 2/2003 | Igaki |
| 2003/0039689 A1 | 2/2003 | Chen et al. |
| 2003/0065355 A1 | 4/2003 | Weber |
| 2003/0093107 A1 | 5/2003 | Parsonage et al. |
| 2003/0105518 A1 | 6/2003 | Dutta |
| 2003/0105530 A1 | 6/2003 | Pirhonen |
| 2003/0108588 A1 | 6/2003 | Chen |
| 2003/0153971 A1 | 8/2003 | Chandrasekaran |
| 2003/0155328 A1 | 8/2003 | Huth et al. |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0234242 A1 | 12/2003 | McCoy |
| 2003/0236563 A1 | 12/2003 | Fifer |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0106987 A1 | 6/2004 | Palasis et al. |
| 2004/0111149 A1 | 6/2004 | Stinson |
| 2004/0126405 A1 | 7/2004 | Sahatjian |
| 2004/0127970 A1 | 7/2004 | Weber |
| 2004/0143180 A1 | 7/2004 | Zhong et al. |
| 2004/0143317 A1 | 7/2004 | Stinson et al. |
| 2004/0167610 A1 | 8/2004 | Fleming, III |
| 2005/0004663 A1 | 1/2005 | Llanos et al. |
| 2005/0021131 A1 | 1/2005 | Venkatraman et al. |
| 2005/0087520 A1 | 4/2005 | Wang et al. |
| 2005/0111500 A1 | 5/2005 | Harter et al. |
| 2005/0147647 A1 | 7/2005 | Glauser et al. |
| 2005/0157382 A1 | 7/2005 | Kafka et al. |
| 2005/0211680 A1 | 9/2005 | Li et al. |
| 2006/0033240 A1 | 2/2006 | Weber et al. |
| 2006/0120418 A1 | 6/2006 | Harter et al. |
| 2007/0023974 A1 | 2/2007 | Wu |

FOREIGN PATENT DOCUMENTS

| | | |
|---|---|---|
| DE | 44 07 079 | 9/1994 |
| DE | 197 31 021 | 1/1999 |
| DE | 198 56 983 | 12/1999 |
| DE | 29724852 | 2/2005 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0583170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0714641 | 6/1996 |
| EP | 0 842729 | 5/1998 |
| EP | 0842729 | 5/1998 |
| EP | 0 970 711 | 1/2000 |
| EP | 1210 922 | 6/2002 |
| GB | 2 247 696 | 3/1992 |
| JP | 4-33791 | 2/1992 |
| JP | 7-124766 | 5/1995 |
| JP | 10-166156 | 6/1998 |
| JP | 2003-53577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 97/18058 | 5/1997 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/38325 | 5/2002 |
| WO | WO 03/015978 | 2/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |

OTHER PUBLICATIONS

Acquarulo et al., *Enhancing Medical Device Performance with Nanocomposite Poly*, Med. Device Link.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal*

Nontoxic Stent and Development of a Stent Placement Device, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).

Fan et al., *Plasma Absorption of Femtosecond Laser Pulses in Dielectrics*, J. of Heat Transfer, vol. 124, pp. 275-283 (2002).

He et al., *Assessment of Tissue Blood Flow Following Small Artery Welding with an Intraluminal Dissolvable Stent*, Microsurgery, vol. 19(3), pp. 148-152 (1999).

Hoffnagle et al., *Design and performance of a refractive optical system that converts a Gaussian to a flattop beam*, Applied Optics, vol. 39, No. 30 pp. 5488-5499 (2000).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

NanoComposix, products, www.nanocomposix.com, downloaded Mar. 26, 2007, 2 pgs.

Nanosilver, Photocatalyst and Nanocomposite Material, http://eng.nanocomposite.net downloaded Mar. 26, 2007, 1 pg.

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Sun et al., "Inert gas beam delivery for ultrafast laser micromachining at ambient pressure", J. of Appl. Physics, vol. 89, No. 12 pp. 8220-8223 (2001).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

von Recum et al., *Degradation of polydispersed poly(L-lactic acid) to modulate lactic acid release*, Biomaterials, vol. 16, pp. 441-445 (1995).

Zhang et al., "Single-element laser beam shaper for uniform flat-top profiles" Optics Express, vol. 11, No. 16, pp. 1942-1948 (2003).

* cited by examiner

METHOD OF REMOVING STENT ISLANDS FROM A STENT

CROSS REFERENCE TO RELATED APPLICATION

This application claims the benefit of and incorporates by reference U.S. Patent Application No. 60/830,208 which was filed on Jul. 11, 2006.

BACKGROUND OF THE INVENTION

1. Field of the Invention

This invention relates to implantable medical devices, such as stents.

2. Description of the State of the Art

A typical stent is a cylindrically shaped device, which holds open and sometimes expands a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

Stents have been made of many materials including metals and polymers. Polymer materials include both nonbioerodable and bioerodable plastic materials. In some applications, a polymeric bioerodable stent may be more advantageous than a metal stent due to its biodegradeability and greater flexibility relative to the metal stent.

The cylindrical structure of a stent is typically composed of a scaffolding that includes a pattern or network of interconnecting structural elements or struts. The scaffolding can be formed from wires, tubes, or planar films of material rolled into a cylindrical shape. Furthermore, the pattern that makes up the stent allows the stent to be radially expandable and longitudinally flexible. Longitudinal flexibility facilitates delivery of the stent and rigidity allows a stent to hold open a lumen of a tubular organ. Generally, the pattern should be designed to maintain the longitudinal flexibility and rigidity required of the stent. The stent should also have adequate strength in the circumferential direction.

A number of techniques have been suggested for the fabrication of metallic and polymeric stents from tubes and planar films or sheets. Examples of such techniques include laser cutting or etching a pattern onto a material. Laser cutting may be performed on a planar film of a material which is then rolled into a tubular configuration. Alternatively, a desired pattern may be etched directly onto a tube. Other techniques involve cutting a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter, and U.S. Pat. No. 5,906,759 to Richter.

Additionally, a polymeric wire may be coiled to form a polymeric stent. In yet another method, a polymeric stent may be formed from a tube by laser cutting a pattern of cylindrical rings and connecting rings in the tube itself. See, e.g., U.S. Pat. No. 6,585,755 to Jackson et al.

"Islands" refer to pieces or portions of metal or polymeric tubing material that are not intended to be part of a stent pattern, and that remain attached to stent struts after laser cutting. The pieces or portions may have a relatively weak physical attachment to a strut or may be wedged between struts with no physical attachment to the struts. Stent islands are conventionally removed from the stent by inserting a metal mandrel through the stent and tapping the mandrel against a surface. This method of removing stent islands after laser cutting the stent causes vibrations that essentially shake the islands out of the stent. However, such vibrations may also damage the stent. In particular, regions of a stent that are exposed to high stress during stent use may be damaged, which may weaken the stent in these high stress regions.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

SUMMARY OF THE INVENTION

Various embodiments of the present invention provides a method and a tool for removing stent islands by blowing a gas stream at or near the islands. The tool is designed to consistently remove stent islands through the use of a pressurized gas. The use of pressurized gas minimizes any damage to the stent.

DETAILED DESCRIPTION OF THE INVENTION

Figure 1:
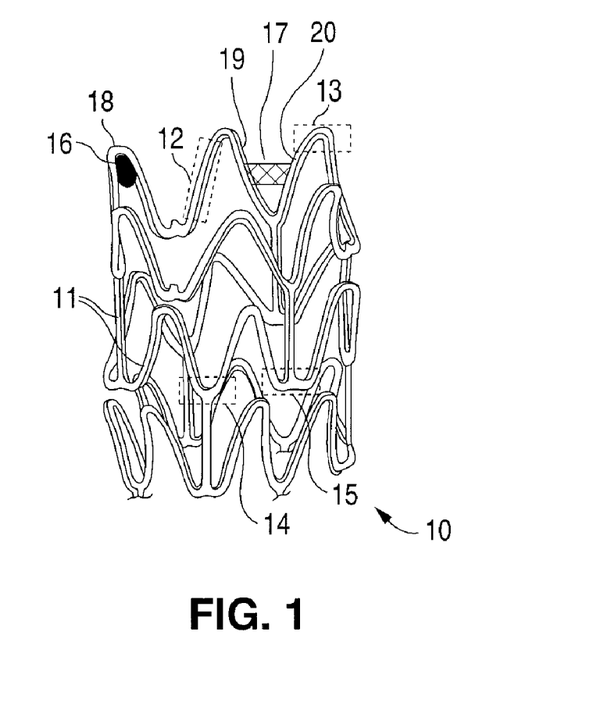
FIG. 1 depicts a stent.

FIG. 1 illustrates a stent 10 that includes a number of interconnecting structural elements or struts 11. In general, the pattern of the stent struts is designed so that stent 10 can be radially compressed and expanded. Stent 10 may include portions of struts that are straight or relatively straight, an example being a straight portion designated by reference numeral 12. Stent 10 may also include portions of struts that are bent, such as the portions designated by reference numerals 13, 14, and 15. Bent portions 13, 14, and 15 may bend further when stent 10 is crimped radially inwardly. Bent portions 13, 14, and 15 may bend further outward when stent 10 is expanded radially outwardly. In some embodiments, a stent such as stent 10 may be fabricated by laser cutting a strut pattern on a tube. In other embodiments, chemical etching may be used to form a strut pattern on a tube.

FIG. 1 depicts exemplary stent islands 16 and 17 formed after laser cutting the stent into a pattern or chemically etching the pattern. Island 16 has a relatively weak physical attachment to a strut 18 and island 17 is wedged between struts 19 and 20. Due to the relatively weak attachment, the invention provides a method and an apparatus for removing such islands by blowing a gas stream at or near the islands. The apparatus and method are designed to consistently remove stent islands through the use of a pressurized fluid such as a gas. The use of pressurized fluids minimizes any damage to the stent.

Embodiments of the present invention include a tube with at least one hole or opening that is adapted to receive a stent thereon. In some embodiments, a stent having islands is mounted over the tube and a fluid conveyed through or into the tube flows out of the hole. The stent with islands is mounted or positioned on the tube hole such that the conveyed fluid flowing through the hole facilitates removal of an island.

Figure 2:
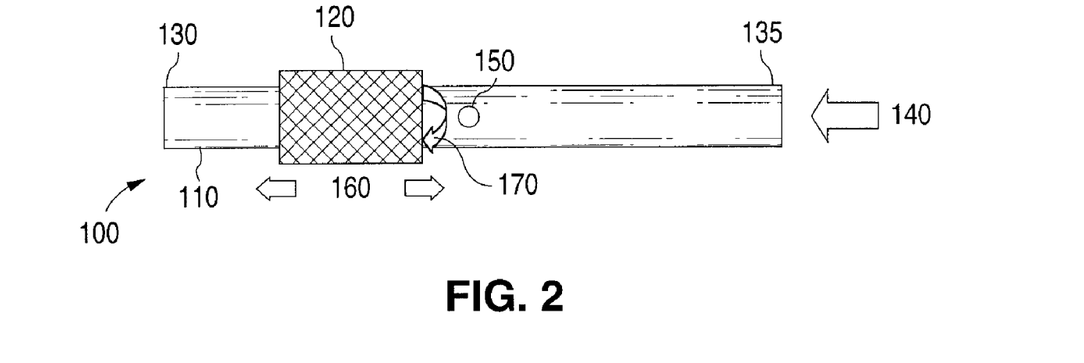
FIG. 2 depicts a stent island removal tool according to an embodiment of the invention.

One embodiment of a stent island removal tool 100 is shown in FIG. 2. Tool 100 is composed of a tube 110 with an outer diameter that is the same or larger than the inner diameter of a stent 120 that is positioned over tube 110. In certain embodiments, stent 120 has a slip fit, meaning stent 120 is slidably mounted to allow axial and rotational movement. One end 130 of the tube may be occluded and the other end 135 is connected to a high-pressure fluid source 140. In another embodiment, both ends of tube 130, 135 may be occluded, and the pressurized fluid 140 would enter from the surface of the tube (not shown). One or more openings 150 are located on the surface of tube 110 to allow the compressed fluid to exit openings 150. In one embodiment, openings 150 are located at other circumferential positions of tube 110. The compressed fluid blows radially through openings 150, blowing the islands off stent 120.

In certain embodiments, stent 120 may be mounted on tube 110 using an interference fit or press fit. In such an embodiment, the outer diameter of tube 110 is the same or substantially the same as the inner diameter of stent 120. The fit is tight enough that the stent does not slide axially or rotate during stent removal.

In several embodiments where stent 120 is slidably mounted, islands in various portions of the stent may be removed by translating the stent axially, as depicted by arrow 160, rotationally as depicted by arrow 170, or both, to remove islands in the various portions of the stent. In other embodiments, tube 110 may be moved axially or rotationally with respect to stent 120 such that the at least one hole may remove islands in various portions of the stent. In further embodiments, both stent 120 and tube 110 are moved with respect to each other. In one embodiment, the relative rotational movement of the stent and tube can be provided by attaching the tube to a fixture that rotates the tube. In another embodiment, relative axial movement of the stent and tube can be provided by attaching the tube to a fixture that vibrates longitudinally. Such a fixture can also rotate the stent to provide both relative rotational and translational motion.

Figure 3A:
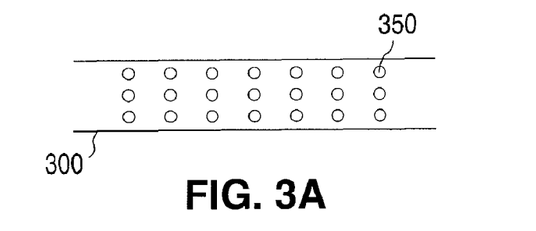
FIGS. 3A-C depict hole patterns according to various embodiments of the invention.
Figure 3B:
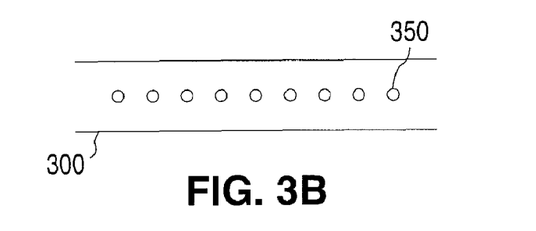
Figure 3C:
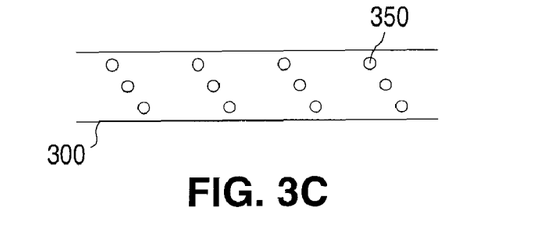

In several embodiments, a tube 300 for removing stent islands may have more than one opening 350, as illustrated in FIGS. 3A-C. The openings may be arranged in different patterns such as circular patterns (3A), longitudinal patterns (3B), or helical (3A), but the patterns are not limited thereto.

Figure 4A:
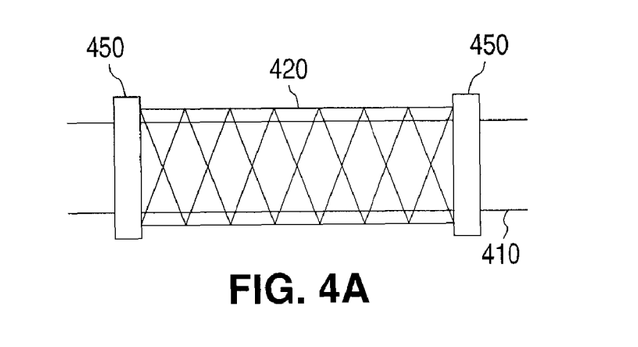
FIGS. 4A-B depict a stent island removal tool according to an embodiment of the invention.
Figure 4B:
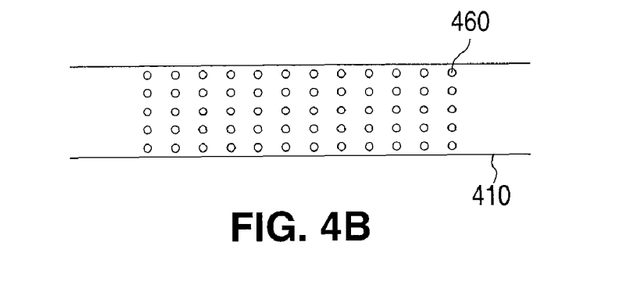

In some embodiments, stent island removal can be performed with little or no relative movement of the stent with respect to the stent island removal tube. FIGS. 4A-B are an illustration of a stationary stent island removal procedure. Holes in tube 410 are not shown for the sake of clarity. Alternatively or additionally, stent 420 has an interference fit with tube 410 such that the stent remains stationary on the tube while the blowing occurs. In some embodiments, rotational and axial movement of stent 420 may be reduced or prevented on tube 410 with collets 450, at the ends of stent 420. Alternatively, only one collet 450 may be used around one end of stent 410 if the other end of the stent is pressed against a stationary portion of the tool. In one embodiments, tube 410 has a sufficient number of holes such that all or most of the islands on the stent are removed. FIG. 4B depicts tube 410 showing a high density of holes 460. In other embodiments, the holes are in a pattern coincident with the likely location of stent islands for a given stent pattern. Different stent patterns may require different tube hole patterns.

The force of the fluid through the holes should be large enough to remove a stent island. Force depends on the flow rate of the fluid conveyed into the tube, and the pressure of the fluid in the tube. If a compressible fluid, such as a gas is used, then the temperature of the gas is an additional factor in determining the force out of the tube. The force of the gas should not be high enough such that it causes damage to the stent. Because the islands may vary in size, different sized holes may be necessary. The size of the holes should be determined relative to the islands and width of the struts. In several embodiments, the size of the holes is determined such that the force per unit area applied on the islands is high enough to remove the island, but not so high as to damage the surrounding struts. If the hole is smaller, then a higher force may be necessary to remove the islands.

The method of removing stent islands can include multiple passes of the stent over the gas flowing from the opening(s). The gas flow the flow can be continuous, variable, or pulsed by controlling the gas supply. Continuous flow is a constant flow over time. A variable flow is a changing flow over time. A pulsed flow is an on-off type of flow, and may be continuous or variable. The pulses may occur at regular intervals, or irregular intervals.

The gas velocity, the gas flow direction, the gas temperature, the gas pulse frequency, etc. can be varied to provide a force needed to remove the stent islands. Various types of gases may be used in the present invention, including but not limited to air, argon, oxygen, nitrogen, carbon dioxide.

In one embodiment, the tube is cooled to make the stent islands more brittle so they may be removed more easily. In another, the gas may be cooled, further cooling the islands. In a further embodiment, both the tube and the gas may be cooled.

Figure 5A:
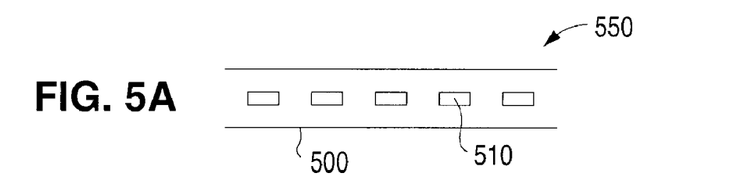
FIGS. 5A-C depict hole opening patterns according to various embodiments of the invention.
Figure 5B:
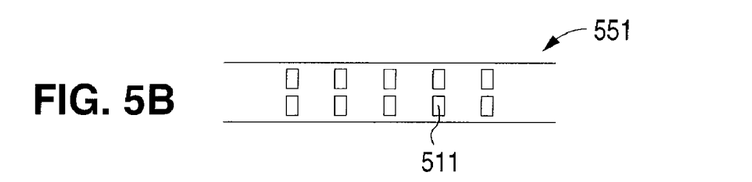
Figure 5C:
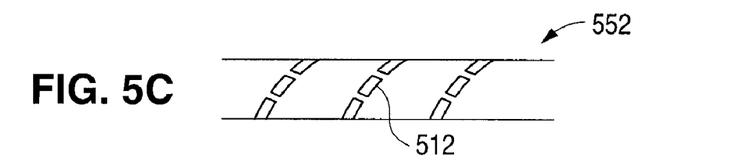

It is also contemplated that the cross-section of the openings can have a variety of shapes. In some embodiments, the shape of the opening can be circular, oval, square, or rectangular. In particular embodiments, the openings may be slits. FIGS. 5A-C depict various arrangements of slits in a tube. FIG. 5A depicts a tube 550 with a pattern of slits 510 arranged axially, with the major axis of the slits 510 aligned with the longitudinal axis. FIG. 5B depicts a tube 551 with a pattern of slits 511 arranged circumferentially, with the major axis of the slits 511 aligned around the circumference of the tube. FIG. 5C depicts a tube 552 with a pattern of slits 512 arranged helically, with the major axis of the slits 512 aligned at an angle to the longitudinal axis. Using a longer rectangular slit may allow the fluid to exit as a thin sheet rather than a point flow of fluid through a circular opening.

Figure 6A:
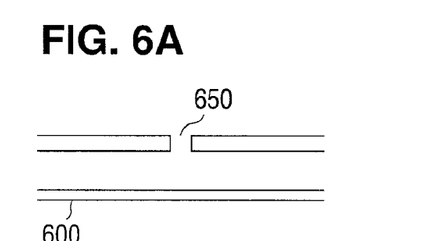
FIGS. 6A-E depict the profiles of holes according to various embodiments of the invention.
Figure 6B:
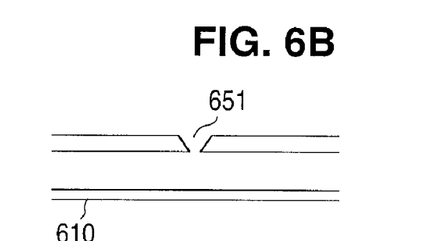
Figure 6C:
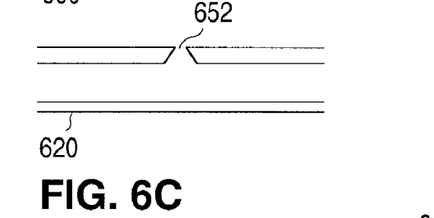

The size of the cross-section of the holes between the inside and outside of the tube can be constant or can vary. FIG. 6A depicts a tube 600 with a hole 610 with a constant cross-section. FIG. 6B-C depict tubes 610 and 620 with holes 651 and 652 having cross-sections that increase and decrease, respectively. Hole 651 acts to disperse fluid flow, while hole 652 acts to concentrate fluid flow.

Figure 6D:
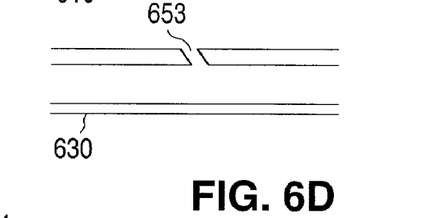
Figure 6E:
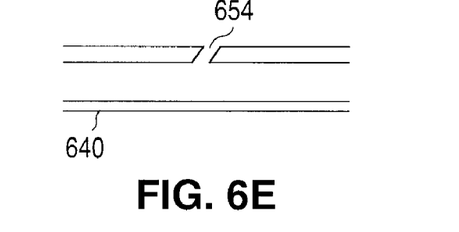

In further embodiments, the holes can be adapted to direct airflow in a selected direction. FIGS. 6D-E depict tubes 630 and 640 with holes 653 and 654 that direct fluid flow at an acute angle to the surface of the tubes.

In several embodiments, the tube is made of metal. In other embodiments, the tube may be made of a polymeric material. The selection of material may be based on operating temperature, pressure, duty cycle, compatibility of the tube material with the stent material or gas, cost, but is not limited thereto. In some embodiments, the tube is stainless steel.

The present invention removes stent islands while maintaining stent integrity. The method and apparatus of the invention can be used to remove metal or polymeric stent islands from stents. Examples of stents for use in the invention include, without limitation, self-expandable stents, balloon-expandable stents, stent-grafts, and vascular grafts.

Polymers for use in fabricating a substrate of a stent or a coating for a stent can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an stent include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A non-polymer substrate of the stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method of removing stent islands, the method comprising:
   positioning a stent over a tube, the stent comprising a pattern and removable islands attached to the pattern not intended to be part of the pattern, wherein the tube includes at least one outlet opening in communication with an interior of the tube;
   conveying a fluid into the tube, wherein the fluid is a gas, wherein the fluid exits through at least one outlet opening, wherein the exiting fluid facilitates removal of at least one of the islands of the stent pattern.

2. The method of claim 1, wherein the pattern is formed by laser cutting.

3. The method of claim 1, wherein the stent is slid along the longitudinal axis of the tube.

4. The method of claim 1, further comprising sliding the stent over more than one opening.

5. The method of claim 1, further comprising sliding the stent back and forth over the tube to facilitate removal of the islands.

6. The method of claim 1, further comprising securing the stent to the tube with retaining members at the ends of the stent.

7. The method of claim 6, wherein the retaining members are collets.

8. The method of claim 1, wherein the stent comprises a biostable and/or bioabsorbable polymer.

9. The method of claim 1, wherein the stent is a metallic stent.

10. The method of claim 1, wherein the fluid flow is continuous.

11. The method of claim 1, wherein the fluid flow is pulsed.

12. The method of claim 1, wherein the at least one opening allows the fluid to exit the tube as a thin sheet.

13. The method of claim 1, wherein the fluid is emitted in a radial direction from the at least one opening in the tube.

14. The method of claim 1, wherein the fluid is emitted in a direction other than radial from the at least one opening in the tube.

15. A method of removing stent islands, the method comprising:

positioning a stent over a tube, the stent comprising a pattern and removable islands attached to the pattern not intended to be part of the pattern, wherein the tube includes at least one outlet opening in communication with an interior of the tube;

conveying a fluid into the tube, wherein the fluid exits through at least one outlet opening, wherein the exiting fluid facilitates removal of at least one of the islands of the stent pattern, wherein the stent is rotated about the longitudinal axis of the tube.

16. A method of removing stent islands, the method comprising:

positioning a stent over a tube, the stent comprising a pattern and removable islands attached to the pattern not intended to be part of the pattern, wherein the tube includes at least one outlet opening in communication with an interior of the tube;

conveying a fluid into the tube, wherein the fluid exits through at least one outlet opening, wherein the exiting fluid facilitates removal of at least one of the islands of the stent pattern,     wherein the stent is rotated about the longitudinal axis of the tube, and slid along the longitudinal axis of the tube.

\* \* \* \* \*